(12) United States Patent
Busin et al.

(10) Patent No.: US 9,295,248 B2
(45) Date of Patent: Mar. 29, 2016

(54) DEVICE, KIT AND METHODS FOR USE IN OPHTHALMOLOGY

(71) Applicants: FONDAZIONE BANCA DEGLI OCCHI DEL VENETO ONLUS, Zelarino (IT); Massimo Busin, Forli (IT)

(72) Inventors: Massimo Busin, Forli (IT); Alessandro Ruzza, Zelarino (IT)

(73) Assignees: FONDAZIONE BANCA DEGLI OCCHI DEL VENETO ONLUS, Zelarino (IT); Massimo Busin, Forli (IT)

( * ) Notice: Subject to any disclaimer, the term of this patent is extended or adjusted under 35 U.S.C. 154(b) by 0 days.

(21) Appl. No.: 14/359,443

(22) PCT Filed: Nov. 21, 2012

(86) PCT No.: PCT/EP2012/073208
§ 371 (c)(1),
(2) Date: May 20, 2014

(87) PCT Pub. No.: WO2013/076130
PCT Pub. Date: May 30, 2013

(65) Prior Publication Data
US 2015/0150242 A1  Jun. 4, 2015

Related U.S. Application Data

(63) Continuation of application No. 13/301,736, filed on Nov. 21, 2011.

(51) Int. Cl.
*A01N 1/02* (2006.01)
*A61F 2/16* (2006.01)
*A61F 2/14* (2006.01)

(52) U.S. Cl.
CPC ............ *A01N 1/0278* (2013.01); *A01N 1/0263* (2013.01); *A61F 2/1691* (2013.01); *A61F 2/145* (2013.01)

(58) Field of Classification Search
CPC ..... A61F 2/145; A61F 2/1678; A61F 2/1691; A61F 9/00; A61F 9/0017; A01N 1/00263
See application file for complete search history.

(56) References Cited

U.S. PATENT DOCUMENTS 3,091,328 A  5/1963  Leonardos
4,093,291 A  6/1978  Schurgin
(Continued)

FOREIGN PATENT DOCUMENTS

EP   1 857 074    11/2007
WO   2007-132332  11/2007
(Continued)

OTHER PUBLICATIONS

Busin et al. "A modified technique for Descemet membrane stripping automated endothelial keratoplasty to minimize endothelial cell loss" *Archives of Ophthalmology*, vol. 126, No. 8, pp. 1133-1137 (Aug. 2008).

(Continued)

*Primary Examiner* — Thomas McEvoy
*Assistant Examiner* — Julie A Szpira
(74) *Attorney, Agent, or Firm* — Nixon & Vanderhye PC

(57) ABSTRACT

The present invention refers to a device and a kit for the shipment and preservation of corneal lenticules ready for use in a lamellar keratoplasty surgery. The device (1) comprises a first open portion (2), apt to receive and contain the lenticule, and a fenestrated lid (10) to close said first portion. The device further comprises a second portion (3) of substantially tubular shape with a diameter lower than the diameter of the lenticule. The device may further comprise a third portion (7) apt to be reversibly connected to a grip means. The fenestrated lid and the front opening (5) allow preservation fluid to nourish the lenticule tissue during the preservation and/or the shipment. The present invention also refers to a method for preserving, shipping and prearranging the lenticules so as to facilitate posterior lamellar keratoplasty surgery (or endokeratoplasty).

10 Claims, 3 Drawing Sheets

(56) References Cited

U.S. PATENT DOCUMENTS

| | | |
|---|---|---|
| 4,257,521 A | 3/1981 | Poler |
| 4,423,809 A | 1/1984 | Mazzocco |
| 4,750,610 A | 6/1988 | Ryder |
| 4,844,242 A | 7/1989 | Chen et al. |
| 5,779,711 A | 7/1998 | Kritzinger et al. |
| 6,183,513 B1 | 2/2001 | Guenthner et al. |
| 6,280,449 B1 * | 8/2001 | Blake ............................ 606/107 |
| 6,789,544 B2 | 9/2004 | Busin |
| 6,955,432 B2 | 10/2005 | Graham |
| 2004/0059360 A1 | 3/2004 | Busin |
| 2006/0212041 A1 * | 9/2006 | Nigam ............................ 606/107 |
| 2009/0204122 A1 | 8/2009 | Ichinohe et al. |
| 2010/0211051 A1 | 8/2010 | Weston et al. |
| 2011/0166650 A1 | 7/2011 | Busin |
| 2011/0245840 A1 | 10/2011 | Seyboth et al. |
| 2012/0289969 A1 | 11/2012 | Seyboth et al. |
| 2013/0130222 A1 | 5/2013 | Ruzza et al. |

FOREIGN PATENT DOCUMENTS

| | | |
|---|---|---|
| WO | 2008-155748 | 12/2008 |
| WO | 2009/050511 | 4/2009 |

OTHER PUBLICATIONS

Busin et al. "Pneumatic dissection and storage of donor endothelial tissue for Descemet's membrane endothelial keratoplastry" *Ophthalmology*, vol. 117, No. 8, pp. 1517-1520 (Aug. 2010).

Dapena et al. "Standardized 'no-touch' technique for Descemet mwembrane endothelial keratoplasty" *Archives of Ophthalmology*, vo. 129, No. 1, pp. 88-94 (Jan. 2011).

Int'l Search Report for PCT/EP2012/073208, five pages (Apr. 2013).

Written Opinion for PCT/EP2012/073208, six pages (Apr. 2013).

Int'l Preliminary Report on Patentability for PCT/EP2012/073208, four pages (Dec. 2013).

* cited by examiner

DEVICE, KIT AND METHODS FOR USE IN OPHTHALMOLOGY

This application is the U.S. national phase of International Application No. PCT/EP2012/073208, filed 21 Nov. 2012, which designated the U.S. and claims priority to Application No. 13/301,736, filed 21 Nov. 2011, pending; the entire contents of each of which are hereby incorporated by reference.

The present invention refers to a device and a kit for the shipment and the preservation of corneal lenticules ready for use in lamellar keratoplasty surgeries. The present invention also refers to a method for preserving, shipping and prearranging the lenticules so as to facilitate posterior lamellar keratoplasty (or endokeratoplasty) surgeries.

STATE OF THE ART

It is known that several cases of dysfunction of the corneal endothelium are not treated by penetrating keratoplasty (corneal transplant) anymore. Improvement of surgical procedures allows in fact a more conservative treatment, known as anterior or posterior lamellar keratoplasty. In the second case, the posterior part of the diseased cornea is replaced with a thin lenticule (or lenticulum) formed by a healthy endothelium, its Descemet's membrane and a thin layer of stroma which makes the preparation firmer and therefore easier to handle (Gorovoy MS et al. 2005). The recipient cornea preserves the epithelium and the stroma (the healthy anterior part) preventing gaps in its general architecture. Thus, the chances of complications (infections, graft rejection) are reduced. One of the difficulties of this surgery is the preparation of the lenticule, which must have an optimum endothelial density to ensure transparency of the cornea, a minimal and anyhow well-defined final thickness in order to avoid inconvenient corneal thicknesses, and a diameter adequate to ensure good visual recovery. In the initial stage of lamellar keratoplasty, lenticules were prepared by the same surgeons. However, a failure in the preparation forced them to cancel or postpone surgery. For this reason, in most cases the preparation of lenticules is currently performed by Eye Banks, which ensure constant and well-characterized preparations (Terry et al. 2009, Rose L. et al. 2008).

For the preparation of lenticules used in posterior lamellar keratoplasty, corneas stored in Bank laboratories are used.

Nowadays, Eye Banks follow the following procedure: the cornea is placed in an artificial chamber which allows horizontal sectioning of the former with a microkeratome. Corneal epithelium (corresponding to the most superficial part, facing the exterior of the eye) is removed by gentle scraping. Human cornea thickness is of 0.5 mm. From its anterior part a layer of about 0.35 mm is removed by microkeratome. Therefore, a thin part (0.15 mm) of stroma remains, to which Descemet's membrane and endothelium are annexed. This thin lamella, still attached to the original cornea, is the one that will be sent to the surgeon and used in the keratoplasty.

To improve endothelium preservation, the anterior lamina that had been removed is again laid on the posterior one. The preparation, immersed in the cornea preservation fluid, is sent to the surgeon, who before being able to use the lenticule in the lamellar keratoplasty surgery has to perform two actions: with a specially provided instrument, the surgeon should punch the preparation at the desired diameter, separating it from the remainder of the cornea, and subsequently remove the layer of anterior stroma that had been laid thereon. These two operations not only impose additional steps to the surgeon, but are quite difficult, as they require great experience and an adequate instrumentation not present in all structures which perform suchlike surgeries.

Therefore, the need to facilitate the procedures connected to lenticule transplant surgeries is highly felt.

SUMMARY

Object of the present invention is to provide instruments and methods for optimizing the production, preservation, the shipment and the manipulation of lenticules ready for use in lamellar keratoplasty surgeries.

The present invention is based on a novel device and on the surprising discovery that a posterior corneal lenticule isolated and stored (together with its anterior portion) in the device of the present invention even for more than one week maintains the suitability features for use in endokeratoplasty surgeries.

Object of the present invention is a device 1 for the preservation and the shipment of an isolated corneal lenticule, comprising:
   a first open portion 2, apt to receive and contain said lenticule;
   a fenestrated lid 10 apt to close said first portion 2;
   a second portion 3 of a substantially tubular shape with a diameter smaller than the diameter of said lenticule, having a first open end 4 and a second open end 5 connected to said first portion 2 via a connecting portion 6, so as to form a single container body.

A second object of the invention is a kit for the preservation and the shipment of isolated corneal lenticules, comprising:
   a device according to the present invention;
   grip means 8 apt to manipulate said device;
   a sterilizable and sealable container 9 of dimensions such as to contain said device and suitable for the shipment.

A third object of the invention is a method of preparing, preserving and supplying or distributing, from an eye bank to the operating room, a corneal lenticule for use in a lamellar keratoplasty surgery, comprising the following steps:
a) preparing the anterior and posterior lenticules isolated from a cornea isolated at a structure dedicated thereto;
b) arranging the anterior and posterior lenticules inside the device 1 according to claim 1, so as to have the stromal face of the anterior lenticule adhere to the internal wall of said device and the endothelial face of the posterior lenticule facing the lumen of the device, and closing the fenestrated lid which seals rearwards the device.
c) immersing said device containing said lenticule into a (sealable) container comprising a suitable preservation solution;
d) transferring the container containing the device and the lenticule ready for use to the operation room.

A fourth object of the invention is a method for the preparation and preservation of a corneal lenticule for use in a lamellar keratoplasty surgery, comprising the following steps:
a) preparing the anterior and posterior lenticules isolated from a cornea isolated at a structure dedicated thereto;
b) arranging the anterior and posterior lenticules inside the device of the present invention so as to have the anterior lenticule adhere to the internal wall of said device and the endothelial face (of the posterior lenticule) facing the lumen of the device;
c) immersing said device containing said lenticule into a (sealable) container comprising a suitable preservation solution;
d) preserving the lenticule until use.

According to some of its embodiments, the invention entails the following advantages: Lenticule preparation takes place in a dedicated structure, therefore is more accurate. Lenticule preservation and shipment by the kit of the invention, in a form already ready for use, are simple and safe. The surgeon's task is simplified, as he/she just has to recover from the device, and with the latter insert only the posterior lenticule into the patient's eye. Another advantage is, obviously, a reduction of surgical times, as the surgeon receives a preparation already ready for use. Last but not least, the economic advantage. The surgeon and/or the hospital structure will no more need to acquire apparatuses required to perform the punching.

DETAILED DESCRIPTION OF THE INVENTION

Figure 1:
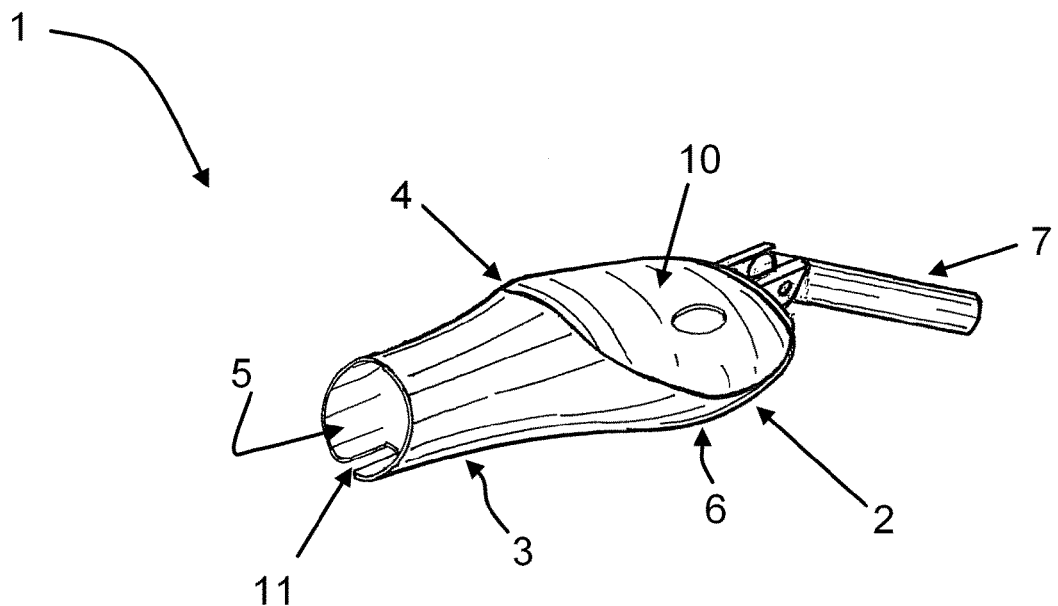
FIG. 1 is a general perspective view of a preferred embodiment of the device according to the present invention.

The present invention refers to a device for the manipulation and preservation and the shipment of isolated corneal lenticules, and will hereinafter be described in detail making reference to the above-indicated figures.

Lenticule

Isolated posterior corneal lenticules are formed by a layer of stroma, of a thickness lower than the natural thickness, by Descemet's membrane and by endothelium.

The lenticules are prepared from isolated corneas by a first step in which, by a microkeratome, there are removed the corneal epithelium and part of the anterior stroma, which subsequently can be repositioned in its seat, and by a subsequent punching step in which the lenticules are cut at the desired diameter (usually 8 to 9 mm). The posterior lenticule, once separated from its anterior part, can be used in endokeratoplasty surgeries. Endokeratoplasty surgeries are cornea repairing surgeries in which only altered posterior layers are replaced, without transplant of the entire cornea.

Keratoplasty Surgeries

In penetrating keratoplasty (PK), cornea is replaced in all its thickness; from a donor's cornea, by punching, a cylindrical portion of tissue is obtained having an average diameter of 8.5 mm and a physiological thickness of 0.5 mm.

Lamellar keratoplasty: a surgical technique involving replacement of a single portion of the cornea, subdividing into:

ANTERIOR lamellar keratoplasty (LK): in this surgical technique only the most anterior part of the cornea, (essentially comprised of stroma) is replaced, by preparation of an anterior lenticule.

POSTERIOR lamellar keratoplasty: the technique is more commonly denominated endokeratoplasty (EKP), and involves the replacement of the posterior portion of the cornea comprised of endothelium, of its Descemet's membrane and a thin layer of stroma.

Posterior lamellar keratoplasty or endokeratoplasty (EKP) is a surgical technique which essentially consists in removing from a whole cornea, via a microkeratome, the anterior portion of cornea (thereby creating an actual anterior lenticule). Having removed the anterior portion, free access will be had to the posterior part from which the surgeon will remove the lenticule by punching. The tissue portion thus created (having an average thickness of 0.15 mm and an average diameter of 8.5 mm which will depend on the punch used) will be inserted in the recipient eye.

Lenticule preparation for endokeratoplasty (EKP) in structures dedicated thereto, such as Eye Banks, takes place as follows:

The cornea, isolated and normally stored, assessed and deemed suitable for EKP, is mounted in an artificial chamber, recreating the physiological conditions of the human eye. By using a microkeratome the anterior lenticule, which subsequently will be repositioned in its original seat, is removed.

Once taken out of the artificial chamber the cornea is punched, thereby obtaining two lenticules adhered to each other, which could be stored in the device. The anterior lenticule, having a more rigid structure, will act as support to the posterior one and will prevent the latter from sustaining folding damage during storage.

Device

The device of the present invention is suitable for the preservation and shipment of isolated corneal lenticules; the device is therefore disposable and consisting in any one sterilizable material, like e.g. polypropylene, polycarbonate, polymethylmetacrylate, stainless steel, so as to be suitably sterilized before use. The device has dimensions suitable for housing the lenticule thereinside, e.g. a length of about 1.5 cm and a width of about 1 cm.

The device comprises a first open portion 2, apt to receive and contain the lenticule. Said first portion 2 could be of any one shape or dimension suitable to allow that the corneal lenticule be laid therein without being damaged. Said first portion could be, e.g., of circular shape with a diameter of about 1 cm.

The device further comprises a fenestrated lid 10 apt to close said first portion 2. The fenestrated lid 10 serves to prevent the coming out of the lenticule itself, and concomitantly to allow the preservation fluid to nourish the lenticule tissue during the preservation and/or the shipment. In the present description, by the term "fenestrated lid" it is meant a lid having an opening allowing transit of the preservation fluid of the solution.

The device further comprises a second portion 3 of substantially tubular shape, e.g. of cylindrical or frustoconical shape. The diameter of said second portion will be lower than the diameter of the lenticule that is to be stored and shipped, e.g. of a diameter of about 0.5 cm. The second portion has a first open end 4 and a second open end 5 connected to the first portion 2 via a connecting portion 6 so as to form a single container body. The connecting portion could have a cross section decreasing from the first portion 2 to the second portion 3, so as to facilitate transit of the lenticule from the receiving portion 2 into the tubular portion 3.

Thus the lenticule, after having suitably being laid on the first portion 2, could be introduced inside the container body (by pincers or a suitable spoon).

Upon closing the defenestrated lid, the lenticule could then be stored, until the time of use in the operating room, in suitable containers as described hereinafter.

The device, beside allowing shipment and preservation of the lenticule without altering the morphological properties of the latter, could be used by the surgeon as an "insertor"

directly in the operating room so that the posterior lenticule may be inserted in the receiver's eye. In the present description by the term "insertor" it is meant that the device is used directly to insert the lenticule into the eye of the receiving patient.

Figure 2:
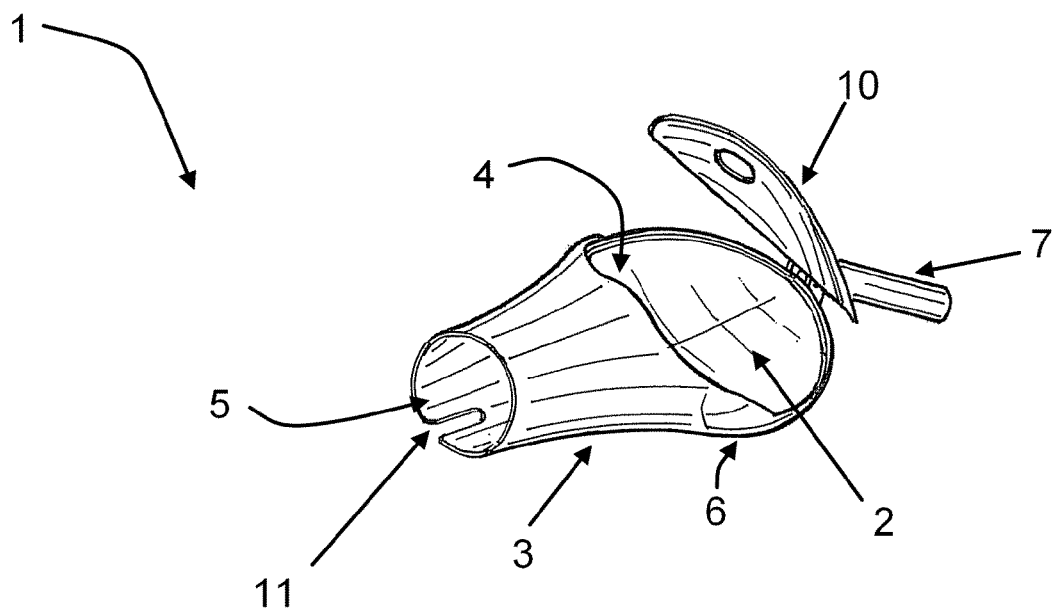
FIG. 2 is the same embodiment of FIG. 1, in which the fenestrated lid is closed.
Figure 3:
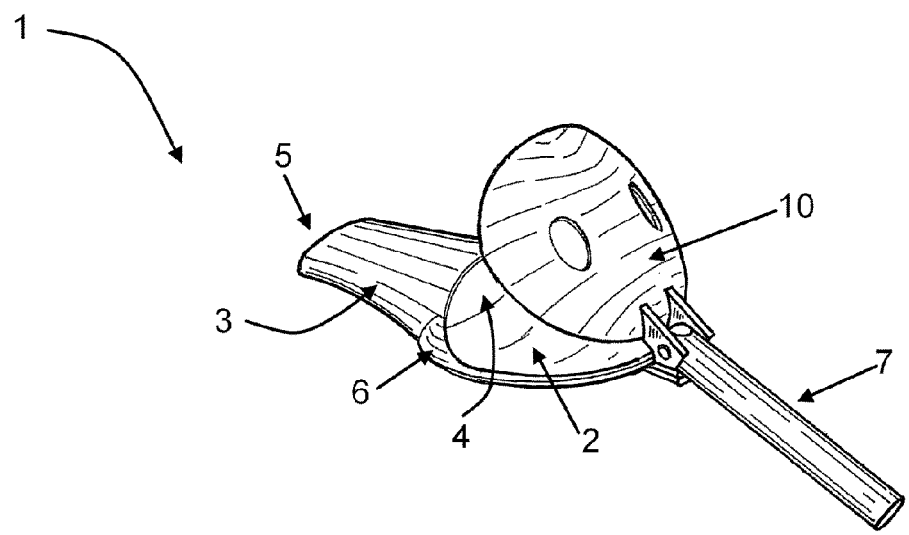
FIG. 3 is a general perspective view of the same embodiment of FIG. 1 and FIG. 2 from a different angle.

In an embodiment as depicted in FIGS. 1-3, the device could further comprise a third portion 7 apt to be reversibly connected to grip means 8. Thus the device, which due to its small dimensions can hardly be handled by the surgeon, could be coupled to the grip means which will allow an easier use thereof. The portion for coupling to the grip means could be, e.g., a pin that will be reversibly inserted into a cylinder.

Always referring to the embodiment shown in FIGS. 1-3, the device could have a groove 11 at the first open end 5 of the device. By this groove 11, it will be facilitated an extraction of the lenticule from the device in use by the surgeon in the operating room.

Kit

The kit for the preservation and the shipment of isolated corneal lenticules subject of the invention comprises:
- a device according to any one of the claims 1 to 3;
- grip means 8 apt to manipulate said device;
- a sterilizable and sealable container 9 of dimensions such as to contain said device and suitable for the shipment.

Containers

The kits in accordance with the invention comprise one or more containers 9, empty or already filled with the solutions described below. Suitable containers are, e.g., containers made of glass, plastics, or any other sterilizable material, provided they are of dimensions such as to be able to contain the device and suitable to be shipped. E.g., the container will comprise internal means for reversibly fastening the device to the container. Examples of fastening means are pins, hooks, cylinders or handles fixed onto the bottom of the container, which will serve to stabilize the device during the preservation and the shipment.

Figure 4:
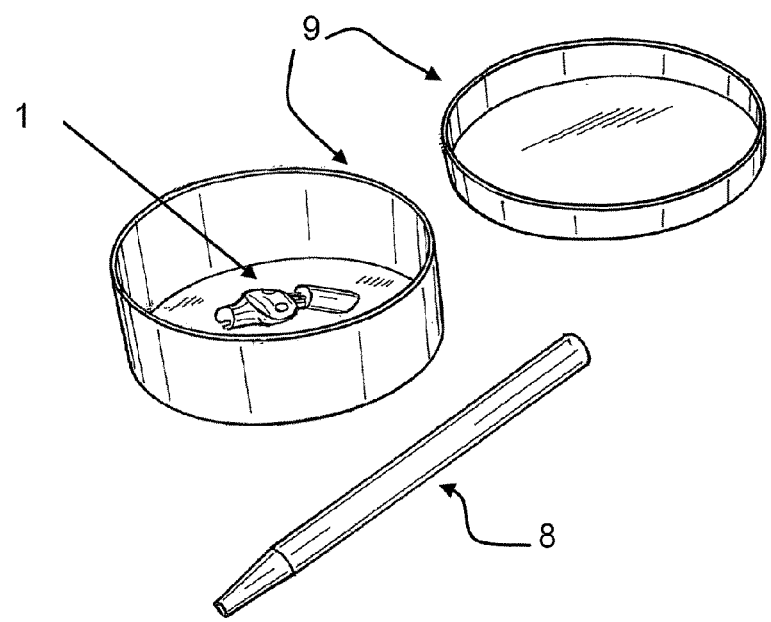
FIG. 4 is a schematic depiction of an embodiment of the kit according to the present invention, showing a container in which the device of FIGS. 1-3 is inserted and the grip means for extracting the device from the container.

In an embodiment, the container of the kit of the present invention could be a sterile flask as shown in FIG. 4.

Grip Means

The kit of the present invention comprises one or more grip means 8 of sterilizable material; said means will be used for the insertion and the extraction of the device from the container of the kit, but also to facilitate the use of the device as "insertor", so that the posterior lenticule may be inserted into the recipient eye. The grip means is, e.g., a handle as shown in FIG. 4, which can be reversibly coupled to the portion 7 of the device suitable to be connected with the handle.

Solution

The sterilizable solution for the preservation of biological material contained in the kit is, e.g., a solution used for the preservation of cell tissues, for instance solutions for in-culture maintaining of cells of human origin. E.g., there could be used solutions comprising L-glutamine, fetal bovine serum, dextran T500, antibiotics and antifungals, sodium pyruvate. Various types of media for the preservation of human corneas are available on the market. Each preservation fluid is tested and validated for the preset object, and is known to a person skilled in the art.

The devices and kits described hereto could be used in the method of the present invention as reported hereinafter.

Transfer Method

Object of the present invention is a method of preparing (setting) and supplying (distributing), from an Eye Bank to the operating room, of a corneal lenticule for use in a posterior lamellar keratoplasty surgery, comprising the following steps:

a) preparing (anterior and posterior) lenticules isolated from a cornea isolated at a structure dedicated thereto;

Lenticule preparing could comprise one or more steps in vitro as described hereto. The procedure begins by horizontally sectioning a cornea isolated by using a microkeratome, thereby making the anterior lenticule that will subsequently be repositioned in its original seat, and, in the last step, the lenticules will be isolated from the remainder of the cornea, through punching.

The preparing takes place in a dedicated structure, e.g. a structure or laboratory internal or external to the eye or cornea bank, fitted with the apparatuses required for the preparing and cutting of corneal lenticules. The corneal lenticule is prepared of the thickness and dimensions suitable for being used in a lamellar keratoplasty surgery. The dimensions and suitable thickness of the lenticule can be standard values known to a person skilled in the art, or values adapted to the needs of the specific patient that will undergo posterior lamellar keratoplasty surgery.

The corneal lenticule thus prepared will be comprised of a layer of stroma, of a thickness lower than the natural thickness, the Descemet's membrane and the endothelium.

In next step b), the (anterior and posterior) lenticules prepared at step a) are arranged inside a device according to the present description.

The lenticule is arranged so as to have the stromal face of the anterior lenticule adhere to the internal wall of said device and the endothelial face of the posterior lenticule facing the lumen of the device; and closing the fenestrated lid which seals rearwards the device so as to prevent the corning out of the tissue from the seat, of which in the foregoing, during shipment from the eye bank to the surgery site.

In next step c), the device containing the lenticule is immersed into a (sealable) container comprising a suitable preservation solution.

In this step, e.g., the containers, the grip means and the solutions described in the foregoing are used in the kits of the present invention.

Therefore, in this step the device containing the lenticule is placed into a container completely covered by the solution; the latter has free access to the inside via the fenestrated lid of the device and the front opening 5. The system is therefore open, suitable for exchanges between the endothelium and the components of the preservation fluid, dissolved oxygen included.

In next step d), the container containing the device and the lenticule ready for use is transferred to the operating room. Before performing the surgery, the surgeon needs to extract from the device the sole posterior lenticule, which will already be in a correct orientation for use in endokeratoplasty surgery. The surgeon at the time of use has to open the container and extract the device from its seat, by using the specially provided grip means 8.

Then, the surgeon with suitable instruments will collect the sole posterior lenticule from the preservation zone 3, so as to let the lenticule slide inside the eye of the receiving patient.

Preservation Method

Object of the present invention is also a method for the preparation and preservation of a posterior corneal lenticule for use in a endokeratoplasty surgery. The preservation method comprises steps a), b) and c) as described in the foregoing. Experimental tests reported hereinafter demonstrated that the lenticule thus prepared is not damaged even after having been stored for more than two weeks.

EXAMPLES

Lenticule Stability
1. Lenticule Preparation and Storage in the Device

Posterior lamellar grafts were prepared as described from 30 human corneoscleral rims unsuitable for penetrating keratoplasty because of insufficient cell density or serological reason. The donor tissue with its wide scleral rim was mounted in an artificial anterior chamber (Moria, Antony, France) and the epithelium was carefully piled off. The initial intrachamber pressure was initially set at 50 mm Hg (Schiotz tonometer) but before sectioning it was increased to 90-100 mm Hg. A Moria microkeratome equipped with either a 300- or 350-μm depth blade, depending on the thickness of the cornea, was passed over the tissue with a targeted posterior lamella thickness of about 150 μm. At the end, the anterior lamellar corneal tissue was again juxtaposed to the stromal face of posterior lenticule and the preparation was transferred to a standard cutting block, to be trephined, endothelial side up, at the diameter of 8.5 mm.

The lenticule with its endothelial face up is gently driven inside the device of the present invention using the protruding surface. After its insertion, the lenticule is moved on the short surface of the container to favor its right position when the container is immersed in the preservation fluid and the protruding part floats close to the surface. The device containing the tissue is transferred to the container filled with 10 ml of a medium composed of MEM-Earle supplemented with 25 mM Hepes, 26 mM Na bicarbonate, 5.5 mM glucose, 2 mM L-glutamine, 1 mM pyruvate, 2% (v/v) of new born calf serum and 6% (wt/vol) of dextran 500. Upon the arrival to the surgeon, the lenticule can be easily extracted through the major opening of the container. The protective anterior lamellar tissue is removed and the lenticule is ready to be inserted into the recipient cornea deprived of the Descemet's membrane and damaged endothelium.

2. Endothelial Cell Evaluation

The endothelial layer of corneas and lenticules was exposed to a hypotonic sucrose solution to evaluate the number of endothelial cells and their general organization. The nuclei of non viable cells were stained with 0.25% (wt/vol) trypan blue. The cell number was estimated at a magnification of 200× with the help of a 10×10 calibrated graticule mounted in the ocular of the microscope (fixed frame technique). The endothelial cell density was expressed as the mean of five different counts, each performed in a different endothelial region. The endothelium was then exposed for 2-3 minutes to 0.2% (wt/vol) alizarin red sodium sulfonate solution to visualize for the cell borders.

3. Glycolysis Evaluation

Glucose was tested in the incubation medium after phosphorylation to glucose-6-phosphate and oxidation by glucose-6-phosphate dehydrogenase and NADP. The resulting NADPH was measured at 340 nm (Boehringer Mannheim/R-Biopharm, Kit N° 10716251035). Determination of NADH was also used to measure the formation of lactate in the medium after its oxidation to pyruvate by NADP and lactate dehydrogenase (Boehringer Mannheim/R-Biopharm, Kit N° 10139084035).

4. Results

Figure 5:
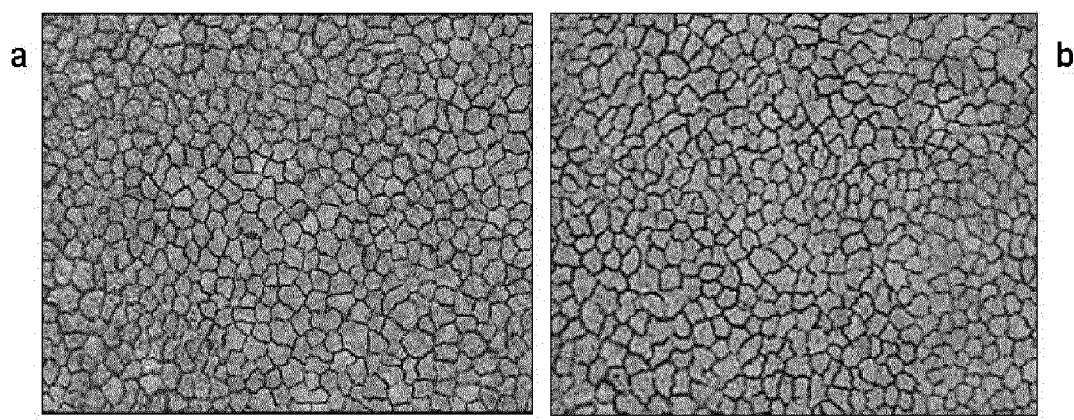
FIG. 5 depicts the endothelial organization in a lenticule stored 7 days inside the device of the present invention. Staining with 0.2% alizarin, magnification (200×): (a) in-culture storage outside the device, (b) storage inside the device.

The effectiveness of container in preserving the endothelium is demonstrated by the unchanged cell density after a storage of seven days (Table 1). Cell mortality was undetectable in all tested samples. The thickness of the lenticulum was directly measured using a sensitive mechanical pachymeter obtained by a modification of a Mitutoyo (Japan) thickness gauge, based on a spring-loaded spindle (Salvalaio et al. Ottica fisiopat 2010; XV: 43-51). These tests indicated that the lenticules did not swell provided dextran is present in the preservation medium (Table 2). A thickness of 170 μm at the end of storage is adequate for successfully performing DSAEK surgery. A further indication of optimal endothelial preservation was provided by the rate of glycolysis that was unchanged in comparison with that of a tissue stored without the support (Table 3). The ratio between the production of lactate and the uptake of glucose demonstrated that glucose was metabolized by aerobic glycolysis, a metabolic pathway normally used by the corneal endothelium. In agreement with these results, the morphological analysis at the end of preservation showed that the storage inside the device did not change the endothelial organization (FIG. 5).

Our control tests to this purpose included the control of endothelial cell density that did not decrease with respect the initial value, the measurement of thickness at the end of preservation that excluded the swelling of the graft, the analysis of glucose uptake and metabolism during the storage that indicate a physiological metabolic flow during the storage. In agreement, the morphological analysis confirmed the optimal preservation of the endothelial organization.

TABLE 1

Cells density

| | Pre-section | Post-section | After 7 days |
|---|---|---|---|
| Endothelial cell density (cells mm$^2$) | 2359 ± 412 (n = 17) | 2359 ± 412 (n = 17) | 2106 ± 417 (n = 17) |
| Endothelial cell density preserved with Device (cells mm$^2$) | 2440 ± 490 (n = 10) | 2440 ± 490 (n = 10) | 2200 ± 503 (n = 10) |

TABLE 2

Stroma Thickness

| | Post-section | After 7 days |
|---|---|---|
| Thickness (μm) | 163 ± 27 (n = 10) | 173 ± 30 (n = 10) |
| Thickness preserved with Device (μm) | 165 ± 21 (n = 8) | 171 ± 15 (n = 8) |

TABLE 3

Rate of glycolisis after 7 days of preservation

| | Without Device | With Device |
|---|---|---|
| Glucose uptake (μmol/mg dry weight) | 7.7 ± 2.7 (n = 9) | 7.9 ± 3.2 (n = 10) |
| Lactate production (μmol/mg dry weight) | 12.7 ± 3.5 (n = 9) | 13.2 ± 4.7 (n = 10) |
| Glucose/lactate ratio | 1.7 ± 0.6 (n = 9) | 1.8 ± 0.9 (n = 10) |

Cell mortality (evaluated with 0.25% (wt/vol) trypan blue) was absent in all samples.

The number of cells was evaluated with the help of a 10×10 calibrated graticule mounted in the ocular of the microscope (fixed-frame technique). To this purpose the endothelial surface was exposed to a hypotonic sucrose solution according to standard procedures (Table 1). To avoid the influence of the hypotonic treatment on thickness the count of endothelial cells and the measurement of final thickness were performed in separate samples (Table 2). Glucose and lactate were tested in the medium using the following enzymatic kits: Boe-

REFERENCES

Gorovoy M S, Price F W (2005) *New technique transforms corneal transplantation*, Cataract and Refractive Surgery Today, November/December 2005, 55-58. Terry M A, Shamie N, Chen E S, Phillips P M, Hoar K L, Friend D J (2009) *Precut tissue for Descemet's stripping automated endothelial keratoplasty*. Ophthalmology 116, 248-256.
Rose L, Briceno C A, Stark W J, Gloria D G, Jun A S (2008) *Assessment of Eye Bank-prepared posterior lamellae corneal tissue for endothelial keratoplasty*. Ophthalmology 28, 695-704.
Salvalaio G, Prosperi G, Busin M, Ruzza A, Frigo A C, Ponzin D. Cheratoplastica lamellare anteriore: determinazione dello spessore dei lenticoli corneali. *Ottica fisiopat* 2010; XV: 43-51.

The invention claimed is:

1. A method of preparing and supplying, from an eye bank to an operating room, a corneal lenticule for use in lamellar keratoplasty surgery, comprising:
    (a) preparing anterior and posterior lenticules, isolated and overlapped, from a cornea isolated at a structure dedicated thereto;
    (b) arranging the anterior and posterior lenticules inside a device comprising: a first open portion adapted to receive and contain said lenticules, a fenestrated lid adapted to close said first portion, and a second portion of a substantially tubular shape with a diameter smaller than said lenticules' diameter, and having a first open end and a second open end connected to said first portion via a connecting portion so as to form a single container body, wherein the device has a groove at said first open end; so as to have the stromal face of the anterior lenticule adhere to the internal wall of said device and the endothelial face of the posterior lenticule facing the lumen of the device, and closing the fenestrated lid which seals rearwards the device;
    (c) immersing said device containing said lenticules into a sealable container comprising a suitable preservation solution; and
    (d) transferring the container containing the device and the lenticules ready for use to the operating room.

2. The method according to claim 1, wherein at preparation stage (a) the prearranged isolated lenticule has a thickness comprised between 8 mm and 9 mm.

3. The method according to claim 1, wherein at preparation stage (a) the prearranged isolated lenticule has a thickness adapted to the needs of a specific patient.

4. The method according to claim 1, wherein preparation stage (a) comprises:
    (i) horizontally sectioning an isolated cornea with a microkeratome; and
    (ii) isolating, through punching of the horizontal section of cornea, the isolated lenticule.

5. The method according to claim 1, wherein the isolated lenticule consists of a stromal layer having a thickness less than natural thickness, Descemet's membrane and endothelium.

6. The method according to claim 1, wherein the device further comprises a third portion adapted to be reversibly connected to said grip means.

7. A method for preparation and preservation of a corneal lenticule for use in lamellar keratoplasty surgery, comprising:
    (a) preparing anterior and posterior lenticules isolated and overlapped from a cornea isolated at a structure dedicated thereto;
    (b) arranging the anterior and posterior lenticules inside a device comprising: a first open portion adapted to receive and contain said lenticules, a fenestrated lid adapted to close said first portion, and a second portion of a substantially tubular shape with a diameter smaller than said lenticules' diameter, and having a first open end and a second open end connected to said first portion via a connecting portion so as to form a single container body, wherein the device has a groove at said first open end; so as to have the anterior lenticule adhere to the internal wall of said device and the endothelial face of the posterior lenticule facing the lumen of the device, and closing the fenestrated lid;
    (c) immersing said device containing said lenticules into a sealable container comprising a suitable preservation solution; and
    (d) preserving the lenticules until use.

8. The method according to claim 7, wherein at preparation stage (a) the prearranged isolated lenticule has a thickness comprised between 8 mm and 9 mm.

9. The method according to claim 7, wherein at preparation stage (a) the prearranged isolated lenticule has a thickness adapted to the needs of a specific patient.

10. The method according to claim 7, wherein the device further comprises a third portion adapted to be reversibly connected to said grip means.

* * * * *